(12) United States Patent
Naisberg et al.

(10) Patent No.: US 7,239,919 B2
(45) Date of Patent: Jul. 3, 2007

(54) DIAGNOSIS, TREATMENT AND RESEARCH OF MENTAL DISORDER

(75) Inventors: Yakov Naisberg, Haifa (IL); Avraham Weizman, Tel-Aviv (IL); Alexander Grinshpoon, Tel-Aviv (IL)

(73) Assignee: Biophysical Mind Technologies, Ltd., Haifa (IL)

( * ) Notice: Subject to any disclaimer, the term of this patent is extended or adjusted under 35 U.S.C. 154(b) by 577 days.

(21) Appl. No.: 10/476,099

(22) PCT Filed: Apr. 23, 2002

(86) PCT No.: PCT/IL02/00322

§ 371 (c)(1), (2), (4) Date: Oct. 24, 2003

(87) PCT Pub. No.: WO02/087410

PCT Pub. Date: Nov. 7, 2002

(65) Prior Publication Data

US 2004/0138720 A1    Jul. 15, 2004

(51) Int. Cl.
*A61N 1/06* (2006.01)
(52) U.S. Cl. .......... 607/45; 600/544; 600/545
(58) Field of Classification Search ........... 607/45; 600/544, 545
See application file for complete search history.

(56) References Cited

U.S. PATENT DOCUMENTS

| | | |
|---|---|---|
| 4,275,743 A | 6/1981 | Hjort |
| 4,424,816 A | 1/1984 | Callahan et al. |
| 4,610,259 A * | 9/1986 | Cohen et al. ........... 600/544 |
| 4,646,744 A | 3/1987 | Capel |
| 4,819,648 A | 4/1989 | Ko |
| RE33,590 E | 5/1991 | Dory |
| 5,052,391 A | 10/1991 | Silberstone et al. |
| 5,061,234 A | 10/1991 | Chaney |
| 5,299,569 A | 4/1994 | Wernicke et al. |
| 5,342,410 A | 8/1994 | Braverman |
| 5,501,704 A | 3/1996 | Chang et al. |
| 5,514,175 A | 5/1996 | Kim et al. |
| 5,540,734 A | 7/1996 | Zabara |
| 5,540,736 A | 7/1996 | Haimovich et al. |
| 5,584,297 A | 12/1996 | Bodo et al. |

(Continued)

FOREIGN PATENT DOCUMENTS

WO    WO 95/02360 A1    1/1995

*Primary Examiner*—Robert E. Pezzuto
*Assistant Examiner*—Deborah Malamud
(74) *Attorney, Agent, or Firm*—Frishauf, Holtz, Goodman & Chick, P.C

(57) ABSTRACT

A method and a Cranial Electrical Stimulator CES (4) for operation in a diagnosis, treatment, research, and test mode related to mental disorder, are disclosed. Diagnosis is based on a detected condition of passage of an electric signal via a pathway in the brain defined as passing from a first to a second electrode of a pair of electrodes from an array (12) attached to the skull (6) of a patient. Treatment is achieved by injecting a treatment signal in the pathway detected as having a condition.

A practitioner (2) operates a workstation (8) of the CES (4) that controls a signal and routing box SRB (10) generating input signals and receiving output signal from the brain, via the skull (6) and electrodes (12). The PC (14) of the workstation controls signal input, output reception, measurement, display and storage in memory (15).

40 Claims, 3 Drawing Sheets

U.S. PATENT DOCUMENTS

| | | |
|---|---|---|
| 5,601,090 A | 2/1997 | Musha |
| 5,634,939 A | 6/1997 | Kuster et al. |
| 5,752,911 A | 5/1998 | Canedo et al. |
| 5,800,474 A | 9/1998 | Benabid et al. |
| 5,806,517 A | 9/1998 | Gerhardt et al. |
| 5,807,270 A | 9/1998 | Williams |
| 5,899,922 A | 5/1999 | Loos |
| 5,919,144 A | 7/1999 | Bridger et al. |
| 5,954,630 A | 9/1999 | Masaki et al. |
| 5,995,868 A | 11/1999 | Dorfmeister et al. |
| 6,097,980 A | 8/2000 | Monastra et al. |
| 6,115,631 A | 9/2000 | Heyrend et al. |

* cited by examiner

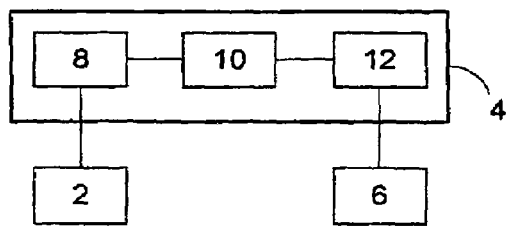
FIG.1
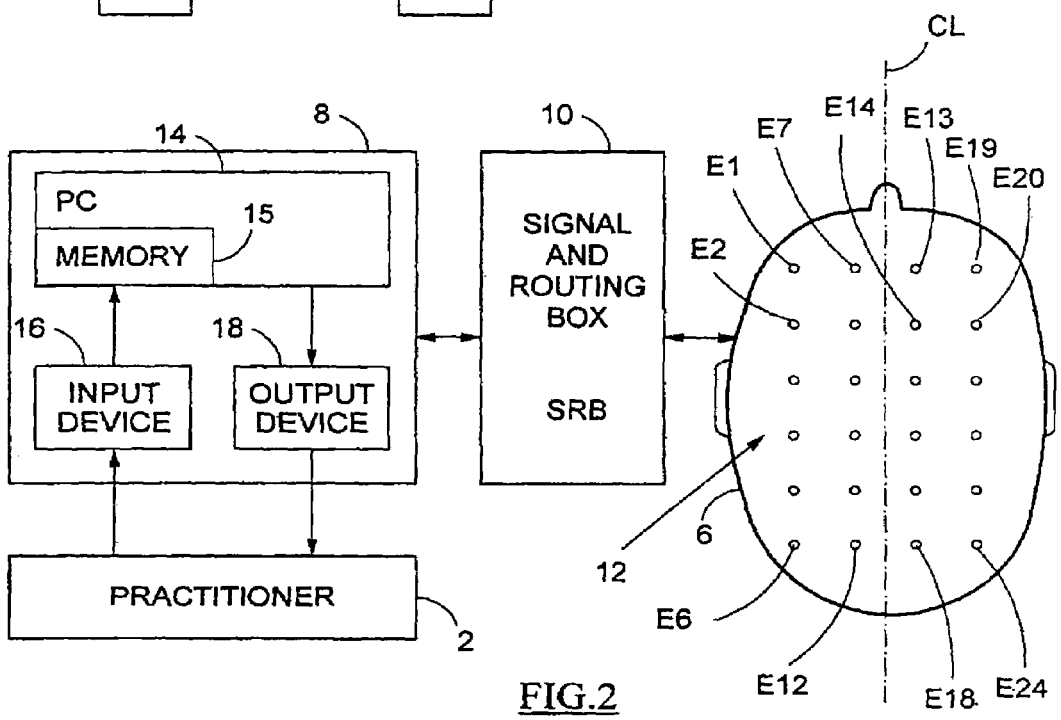
FIG.2
| El.# | max | min | El.# | max | min | El.# | max | min | El.# | max | min |
|---|---|---|---|---|---|---|---|---|---|---|---|
| 1 | | | 7 | | | 13 | | | 19 | | |
| 2 | | | 8 | | | 14 | | | 20 | | |
| 3 | | | 9 | | | 15 | | | 21 | | |
| 4 | | | 10 | | | 16 | | | 22 | | |
| 5 | | | 11 | | | 17 | | | 23 | | |
| 6 | | | 12 | | | 18 | | | 24 | | |
FIG.5

|    | 1   | 2    | 3    | 4    | 5    | 6    | 7    | 8    | 9    | 10 | 11 | 12 | 13 | 14 | 15 | 16 | 17 | 18 | 19     | 20      | 21 | 22 | 23 | 24 |
|----|-----|------|------|------|------|------|------|------|------|----|----|----|----|----|----|----|----|----|--------|---------|----|----|----|----|
| 1  | X   | A1,2 | A1,3 | A1,4 | A1,5 | A1,6 | A1,7 | A1,8 |      |    |    |    |    |    |    |    |    |    |        |         |    |    |    |    |
| 2  | B2;1| X    |      |      |      |      |      | A2,8 |      |    |    |    |    |    |    |    |    |    |        |         |    |    |    |    |
| 3  | B3;1|      | X    |      |      |      |      | A3,8 |      |    |    |    |    |    |    |    |    |    |        |         |    |    |    |    |
| 4  | B4;1|      |      | X    |      |      |      | A4,8 |      |    |    |    |    |    |    |    |    |    |        |         |    |    |    |    |
| 5  | B5;1|      |      |      | X    |      |      | A5,8 |      |    |    |    |    |    |    |    |    |    |        |         |    |    |    |    |
| 6  | B6;1|      |      |      |      | X    |      | A6,8 |      |    |    |    |    |    |    |    |    |    |        |         |    |    |    |    |
| 7  | B7;1|      |      |      |      |      | X    | A7,8 |      |    |    |    |    |    |    |    |    |    |        |         |    |    |    |    |
| 8  | B8;1|      |      |      |      |      |      | X    | A8;9 |    |    |    |    |    |    |    |    |    |        |         |    |    |    |    |
| 9  | B9;1| B9;2 | B9;3 | B9;4 | B9;5 | B9;6 | B9;7 | B9;8 | X    |    |    |    |    |    |    |    |    |    |        |         |    |    |    |    |
| 10 |     |      |      |      |      |      |      |      |      | X  |    |    |    |    |    |    |    |    |        |         |    |    |    |    |
| 11 |     |      |      |      |      |      |      |      |      |    | X  |    |    |    |    |    |    |    |        |         |    |    |    |    |
| 12 |     |      |      |      |      |      |      |      |      |    |    | X  |    |    |    |    |    |    |        |         |    |    |    |    |
| 13 |     |      |      |      |      |      |      |      |      |    |    |    | X  |    |    |    |    |    |        |         |    |    |    |    |
| 14 |     |      |      |      |      |      |      |      |      |    |    |    |    | X  |    |    |    |    |        |         |    |    |    |    |
| 15 |     |      |      |      |      |      |      |      |      |    |    |    |    |    | X  |    |    |    |        |         |    |    |    |    |
| 16 |     |      |      |      |      |      |      |      |      |    |    |    |    |    |    | X  |    |    |        |         |    |    |    |    |
| 17 |     |      |      |      |      |      |      |      |      |    |    |    |    |    |    |    | X  |    |        |         |    |    |    |    |
| 18 |     |      |      |      |      |      |      |      |      |    |    |    |    |    |    |    |    | X  |        |         |    |    |    |    |
| 19 |     |      |      |      |      |      |      |      |      |    |    |    |    |    |    |    |    |    | X      | A19; 20 |    |    |    |    |
| 20 |     |      |      |      |      |      |      |      |      |    |    |    |    |    |    |    |    |    | B20; 19| X       |    |    |    |    |
| 21 |     |      |      |      |      |      |      |      |      |    |    |    |    |    |    |    |    |    |        |         | X  |    |    |    |
| 22 |     |      |      |      |      |      |      |      |      |    |    |    |    |    |    |    |    |    |        |         |    | X  |    |    |
| 23 |     |      |      |      |      |      |      |      |      |    |    |    |    |    |    |    |    |    |        |         |    |    | X  |    |
| 24 |     |      |      |      |      |      |      |      |      |    |    |    |    |    |    |    |    |    |        |         |    |    |    | X  |

FIG. 4

DIAGNOSIS, TREATMENT AND RESEARCH OF MENTAL DISORDER

This application is a U.S. National Phase Application under 35 USC 371 of International Application PCT/IL02/00322 filed Apr. 23, 2002.

FIELD OF THE INVENTION

The present invention relates to mental disorder, and in particular, to the non-invasive diagnosis, treatment and research of mental disorder by application of low alternating current to the skull of a patient.

PRIOR ART

Several patents mention different methods and devices for dealing with mental disorder. U.S. Pat. No. 4,275,743 issued to Hjort, discloses a device and method for measuring the bioelectrical activity of the brain. It describes a better version of EEG (electroencephalograph) and EcoG (electrocorticography).

U.S. Pat. No. 4,424,816 given to Callaham et al., describes a method and a DC apparatus for providing low frequency currents within ranges of 9 Hz to 120 Hz and at least 20 mV to generate an impedance signal for monitoring neurological conditions.

U.S. Pat. No. 4,646,744 granted to Capel, divulges a method and device for treating drug addiction, stress, insomnia and pain with low frequency electric currents within the range of 10 to 35 Hz to 100 Hz and to 200 Hz, with a pulse width of about 1.5 msec.

U.S. Pat. No. 4,819,648 given to Ko, relates to an apparatus and method for using an electromagnetic field to measure localized impedance changes in brain matter and fluid, to diagnose and treat edema connected with head trauma.

U.S. Pat. RE33,590 granted to Dory, deals with a method of using a high frequency electric wave emitter, a main piezoelectric transducer and an echography device for examining and treating local disorders.

U.S. Pat. No. 5,052,391 issued to Silberston et al. provides a method for using high frequency signals in a range of 2.5 to 60 KHz for transcutaneous stimulation by a DC electric device, to block pain sensations.

U.S. Pat. No. 5,061,234 given to Chaney, describes a magnetic neural stimulator and a method for stimulating biological tissues in general.

U.S. Pat. No. 5,342,410 granted to Braverman, deals with an apparatus and method for healing addictions with P300 waves. The periodic electric pulses have a frequency of 50 to 300 Hz and a current amplitude of 0.1 to 60 mA and to 400 mA, a voltage of about 40 to 60 V, with a pulse width of 0.2 to 2 msec, applied for 20 minutes at least.

U.S. Pat. No. 5,501,704 issued to Chang et al. offers a method for treating sleep disorder and a device for using low energy electromagnetic emissions for this kind of therapy. It modulates frequencies within the range 0.1 Hz to 10 KHz U.S. Pat. No. 5,514,175 granted to Kim et al., deals with a method and apparatus for reducing pain sensations and neural dysfunction. It utilizes low and high frequencies in the range of 15 Hz to 15000 Hz.

U.S. Pat. No. 5,540,736 given to Haimovich et al., offers a transcranial electrostimulation apparatus having independent current generators to stimulate the homeostatic endorphinergic midbrain structure with an independently regulated electric current.

U.S. Pat. No. 5,540,734 given to Zabara, offers an apparatus for healing mental disorders with modulating electrical signals to trigeminal and glossopharyngal nerves in the frequency of 5 to 300 Hz and 0.5 to about 20 mA, and pulse width between 0.1 to 1 msec.

U.S. Pat. No. 5,584,297 given to Bodo et al., describes a method and system to measure the cerebral circulation with estimation of the electric activity, rheographic pulse, blood pressure, pulse rate and anxiety level. These measurements being matched with age, height, sex, blood cholesterol, and blood sugar levels.

U.S. Pat. No. 5,634,939 issued to Kuster et al., offers a method and device to treat general anxiety, insomnia and panic attacks with low energy emission therapy. The electric frequency for healing is proposed within the range of 0.1 Hz to 10 KHz for a time exposure from 40 seconds to 15 minutes. In addition, the method uses energy absorption from 100 micro W to 50 W per kilogram of tissue.

U.S. Pat. No. 5,601,090 granted to Musha, deals with a method and device to determine the somatic states of subjects by measuring the scalp potentials, muscle potential, heart-rate, eye-movement, and frequency of eye blinks.

U.S. Pat. No. 5,752,911 issued to Canedo et al., offers a method and device for the treatment of patients with epilepsy by introducing controllable magnetic fields. These fields are generated at a frequency of about 300 Hz and magnetic field intensities ranging from about 0.3 to 0.8 mT, applied from one to several times per week.

U.S. Pat. No. 5,800,474 given to Benabid et al., describes an invasive method and device for applying 10 Hz to 2500 Hz electric current frequencies stimulating the subthalamic nucleus and substantia nigra to reduce epileptic seizures.

U.S. Pat. No. 5,807,270 given to Williams, deals with a brain impedance monitor and method supplying 1 microA AC at 200 Hz frequency. The method has implanted extradural and skin electrodes for measuring oedema states in cases of ischaemia, asphyxia, and trauma.

U.S. Pat. No. 5,806,517 issued to Gerhardt et al., offers a computer-based system for measuring electrochemical operations in the brain to calibrate with carbon, platinum or gold neurotransmitter activities that are assumed to influence mental disorders.

U.S. Pat. No. 5,954,630 granted to Masaki et al., leads to a method and device for using FM theta-inducing audible sound to produce alpha rhythms that are believed to have a therapeutic effect. The device is capable to produce frequencies in the range from 2 Hz to 200 Hz.

U.S. Pat. No. 5,899,922 issued to Loos, leads to an apparatus and method for manipulating the cutaneous nerves with frequencies in the range of 0.1 Hz to 2 Hz and to 45 Hz. The field amplitude is between 1 to 25 V/m. The apparatus is used to aid relaxation, sleep, or sexual arousal and can clinically control the treatment of tremors and seizures.

U.S. Pat. No. 5,919,144 issued to Bridger et al., proposes to measure intracranial pressure with non-invasive frequencies of acoustic signals within the 100 KHz frequencies.

U.S. Pat. No. 5,995,868 granted to Dorfmeister et al., describes a method and apparatus providing information analysis from the brain by electro-encephalogram (EEG) and electro-corticogram (EcoG) for predicting epileptic seizure activity.

DISCLOSURE OF THE INVENTION

The present invention deals with seizure-free low and high frequency electric current application to brain regions and to the measurement of diagnostic parameters of the cranial electrotherapy stimulation (CES) efficacy in monitoring mental and epileptic disorders. Moreover, the invention relates to non-invasive and seizure-free treatment of mental and epileptic patients having abnormal dielectric properties in the neuronal lipid membranes, impaired electric excitability of ion channel matrices and a shifted neurotransmitter turnover leading to defected neuronal electric pathways (NEP's) for biophysical information-processing. The latter cherishes and nurtures the underlying psychopathology of psychiatric disorders.

Today, there is scientific evidence that two anatomically segregated webs, the autonomous neuronal networks (ANN) and the mental neuronal networks (MNN) bind the unifying body-brain-mind interaction executing an electrical synchronizing physiological effect. ANN process inherited negative feedback mechanisms to run four nighttime (one to four stages) and four daytime (five to eight stages) body operational ranges (BOR) of different velocities for biochemicals that have been placed in given biophysical operations.

MNN transform inanimate physical outer informative waves into biophysical-information-processing precisely copying per life event for per unit of time.

When this biophysical information is delivered onto ion channel matrixes, the brain's computer-analog central processing unit displays mind imaging of outer objects or events to create the biophysical mind. All visual, auditory, taste, tactile, and olfactory physical sensorial informative sources behave alike by transforming their information into the biophysical mind units from which mental (Emotional, cognitive and behavior units) operations have been developed.

Normal subjects having homeostatic states secure normal mind and mental operations, which may be electrically identified and recorded.

Deranged operations across ANN and MNN infrastructure result from changes such as in: membrane lipid composition, alteration in shape and density of ion channels, shifting of the electrical threshold of excitable neurons and the turnover of neurotransmitters. Deranged operations share the common characteristic of exerting an inadequate processing of the information to and from memory storages. Special emphasis is placed on the appearance of changes in the NEP's and defective neuronal routes. The latter derail the information-processing direction and distribution causing mental disorders. The biophysical or mind operations run via inappropriate routes of communication delivering biophysical messages to faulty neurons for decoding. Implication is manifested by different forms of mental disorders.

Epilepsy is a very common condition among the neuropsychiatric spectrum of disorders. The association between neuronal structure and inner electrical source development seems to play a crucial role in epilepsy. At present, we may introduce the working hypothesis that massive changes in neuronal lipid formation secondarily may affect the shape and other physical characteristics of pores of ion channels. On the membrane surfaces, such changes create a massive stasis in ion charges that have lost the capacity for an ionic turnover. Such a states secures the emergence of ion charge accumulation.

The underlying stasis prevents message-conductance on certain NEP's. Further, a biophysical massive blockage in ion channels leads to an enhanced ion charge accumulation on both opposite sides of impaired neuronal membranes. Other factors participate as well, causing liquid raise in neuronal membrane lipid organizations influencing neuronal permeability and excitability.

These changes may wax and wane, however gradually leading to an increased amount of ion charges sedimentation rate. It posits that the sedimentation rate gradually reaches the seizure threshold maturation level and spontaneous ionic discharge take place in different directions holding pre-seizure activity. Such a discharge phenomenon is known in medical practice as the "aura". It occurs because of partial pre-seizure discharges having a common denominator. The aura further enhances the sedimentation rate of charges reaching the seizure threshold level beyond which an avalanche-like ionic discharge takes place causing an epileptic fit.

Such epileptic sources may be developed in superficial or deep brain regions all over the brain defining thereby the epileptic symptoms and signs. Epilepsy is a fundamental ionic charge turnover disequilibrium on certain neurons having lost the action potential threshold excitability, and gained a fresh abnormal rise in ion charge accumulation until achieving the culminating seizure threshold activity.

Various neuroimaging evidence shows that brain regions affected by mental and epileptic disorders overlap.

In a pivotal unification, both types of ionic disturbances in mental and epileptic disorders may need the same appropriate diagnostic and treatment means for preventing and correcting the above described electrical disequilibria that occur in neuronal tissues. It must be noticed that such abnormal neuronal tissue will operate under impaired biophysical principles. The latter will operate mainly in the lipid tissue composing about 60% of brain matter that undergoes dielectric changes due to the attracted amount of liquid. It is thus instructive to declare that normal and abnormal regions will have different dielectric properties that may be detected by macroscopic means of measurement applying currents to the scalp.

Far before having this kind of knowledge, medical doctors noticed that harmless electrical currents influence the brain and help in treating stress, depression, anxiety, insomnia, migraine, and several neurological diseases. This type of treatment was introduced as electromedicine under different techniques. Electromedicine extensively used currents applicable to the brain-body regions in the spectrum of low and high frequencies. Consistent with these principles were the a) transcutaneous cranial electrotherapy stimulation (TCES), b) transcutaneous electric nerve stimulation (TENS), c) percutaneous electrical nerve stimulation (PENS) and finally, broadly accepted as cranial electrotherapy stimulation (CES). CES therapy was successfully revived with several methods and devices in the last decade. It became an adjunct method with efficient, safe, convenient, and comfortable outcomes. It seems likely that CES influences the impaired lipid tissues that compose about 60% of brain matter and undergoes dielectric changes in addition to changes in ion channels excitability and neurotransmitters turnover. According to the tenets of electrical application to the brain, one may expect different types of electrical conductivity in relation to different membrane lipid compositions, ion channels in action, and the neurotransmitter turnover.

According to the tenets of electrical application of signals to the brain, one may expect different types of electrical conductivity in relation to different abnormal a) neuronal lipid regions, b) ion channel matrices and c) neurotransmitter turnover. Once this phenomenon is recognized it should be stated that normal and abnormal combinations of neuronal membrane lipid compositions, neurotransmitters, and ion channels provide different electrical conductive measurements from non-invasive current applications. This yields the corresponding diagnostic valuable data that can be obtained during diagnostic monitoring of high frequency currents to the scalp.

Another point worth emphasis is that low frequency currents possess superficial penetration through the scalp, as opposed to high frequency currents that better penetrate deep brain tissue regions. Reflecting over this definition, it is pointed out that high frequency signals passing through neuronal electrical pathways (NEP's) will instantly discharge the ion channels reducing thereby the ion overloaded density of charges that, in turn, will improve the neurotransmitters turnover as well.

The very nature of improved neurotransmitters turnover and ion discharges play a crucial role in improving the liquid balance in lipid membranes leading to the restoration of the electric homeostatic conditions in the previously defective brain regions. Thus, local homeostasis is an expression of better inter-correlation and interconnection of biochemical and biophysical elements, providing the grounds for treatment. It is also preferable to state that in case of epilepsy, the ion discharge reduces the density of ion charges and keeps the overall internal electric sources beyond seizure level to prevent avalanche-like discharges. Consequently, the low and high frequencies of the electrical current provide good attributes for diagnosing and treating mental and epileptic disorders alike. Everything after that is merely instrumental and operational. The crucial argument in favor now state that the old art failed to perceive these physical current advantages and used electrical diagnosis and treatment from another point of view, neglecting the need for improving the available physical parameters to be delivered to the brain paradigm.

Thus, the key concept in the present invention is to simultaneously improve the electric diagnostics and electric treatment by a combined method with a unifying device, to control the applied current properties for optimizing the diagnostic measurements of the cranial electrotherapy stimulation (CES) efficacy in treating mental and epileptic disorders.

SUMMARY

It is an object of the present invention to provide a method for diagnosing mental disorder by injecting electric input signals into and measuring electric output signals from the brain via electrodes (12) arranged in an array comprising a symmetrical electrodes distribution attached to the skull (6) of a patient. The method is characterized by:

operating a diagnostic mode comprising automatic sequential injection of diagnosis input signals in predetermined sequence into combinations of pairs of electrodes chosen from the array of electrodes, measuring output signals from each combination of pairs of electrodes, and displaying the measured signals for detection and diagnosis of mental disorder.

It is another object of the present invention to provide a method for selecting the diagnosis input signal as an alternative current signal with predetermined signal current parameters comprising current amplitude, current frequency and current duration, and measuring output signals from each combination of pairs of electrodes (12) and from each opposite electrodes pair.

It is a further object of the present invention to provide a method wherein:

the current amplitude of the diagnosis input signal is selected to range from 0.1 mA to 5 mA, the current frequency of the diagnosis input signal is selected to range from 2.5 KHz to 250 KHz, the current duration of the diagnosis input signal is selected to range from 1 msec to 500 msec, and an injection delay for insertion between the end and the beginning of two successive diagnosis injection signals is selected from the range spanning from 4 msec to 400 msec.

It is one more object of the present invention to provide a method for measuring an output signal over the pair of electrodes selected for signal injection within a specific injection delay after starting but before ending of the signal injection, and for measuring an output signal over the pair of electrodes opposite to the pair of electrodes (12) injected with the diagnosis signal injection within a specific opposite delay after starting but before ending of the signal injection.

It is yet a further object of the present invention to provide a method for:

measuring diagnosis output signals in dimensions selected from the group of dimensions consisting of voltage, frequency, impedance, resistance and conductance, processing the diagnosis output signals for display, and displaying the diagnosis output signals in association with electrode pair designation for detection and diagnosis of mental disorder.

It is yet another object of the present invention to provide a method for:

operating a treatment mode comprising injecting a treatment input signal in at least one pair of electrodes (12) chosen in accordance with the detection and diagnosis achieved in the diagnosis mode, and selecting the treatment input signal as an alternative current signal with predetermined signal current parameters comprising current amplitude, current frequency and current duration.

It is yet one more object of the present invention to provide a method wherein:

the current amplitude of the treatment input signal ranges from 0.5 mA to 2.5 mA, the current frequency of the treatment input signal treatment is either one of both 50 KHz to 100 KHz, the current duration of the treatment input signal to range from 100 msec to 500 msec, and the injection delay for insertion between the end and the beginning of two successive treatment injection signals injected into two pairs of electrodes (12) out of the least one pair of electrodes ranges from 4 msec to 400 msec.

It is still an object of the present invention to provide a method for:

operating a research mode comprising injecting either one of both a research diagnosis input signal and a research treatment input signal in at least one pair of electrodes (12), selecting the research diagnosis input signal as an alternative current signal with predetermined signal current parameters comprising current amplitude, current frequency and current duration, and measuring research output signals over the electrodes pair (12) injected with the research diagnosis input signal and over the opposite electrodes pair.

It is still another object of the present invention to provide a method wherein the research diagnosis input signal comprises:

a current amplitude selected from the group consisting of 50 microA, 100 microA, 0.5 mA, 1 mA, 2.5 mA and 3 mA, a current frequency selected from the group consisting of 10 Hz, 50 Hz, 100 Hz, 500 Hz, 10 KHz, 25 KHz, 50 KHz, and 100 KHz, current duration from the group consisting of 2 msec, 10 msec, 100 msec, 250 msec and 500 msec, and an injection delay for insertion between the end and the beginning of two successive diagnosis injection signals from the group of delays consisting of a range spanning from 4 msec to 400 msec.

It is still a further object of the present invention to provide a method for:

measuring research diagnosis output signals in dimensions selected from the group of dimensions consisting of voltage, frequency, impedance, and resistance and conductance, processing the research diagnosis output signals for display, and displaying the research diagnosis output signals in association with electrode pair designation for detection and diagnosis of mental disorder.

It is still one more object of the present invention to provide a method for a Cranial Electric Stimulator (4), or CES (4), comprising a diagnosis mode, a treatment mode; a research mode and a test mode and comprising an array of designated electrodes (12) attached in distribution onto the skull (6). The CES (4) is characterized by a workstation (8) operated by a practitioner (2) and coupled to a signal and routing box, SRB (10), to which the array of electrodes is coupled, further comprising in the diagnosis mode:

predetermined alternative current diagnosis input signals generated by the SRB under control of the workstation, for successive injection via all the combinations of pairs of electrodes out of the array of electrodes, wherein each one of pair electrodes defines a path in the brain, for detection of a signal passage condition along a defined path, in the treatment mode:

predetermined alternative current input treatment signals injected for relief of a condition in signal passage paths detected with a condition, in the research mode:

selected alternative current research diagnosis input signals permitting injection into and retrieval of output signals from the brain, and selecting injection of alternative current research treatment input signals, and in the test mode:

the workstation running safety and accuracy checks on the CES (4).

It is still a further object of the present invention to provide a method wherein the diagnosis mode and the treatment mode operate in successive cycles of first diagnosis and next treatment, the treatment mode is operated for adaptive selection of the injected treatment signals according to the detection achieved in the diagnosis mode, and diagnosis output signals are retrieved from the array of electrodes (12), measured and displayed in relation to corresponding designated electrode pairs, for detection of signal passage paths displaying a condition, by comparison to either one and combination of same and previous diagnosis mode session results.

It is still yet another object of the present invention to provide a method wherein an alternative current diagnosis input signals is further characterized by comprising:

a current amplitude of 0.5 mA, a current frequency of 25 KHz and a current duration of 10 msec, and an injection delay of 40 msec being selected for insertion between the end and the beginning of two successive diagnosis input signals injection.

It is still yet a further object of the present invention to provide a method wherein the diagnosis output signals is measured in dimensions selected from the group of dimensions consisting of voltage, frequency, impedance, resistance and conductance, and the diagnosis output signals is processed for display and displayed in association with electrode pair designation, for detection and diagnosis of mental disorder.

It is still yet one more object of the present invention to provide a method wherein the treatment input signal is selected as an alternative current signal with predetermined signal current parameters comprising:

current amplitude selected from the group consisting of current amplitudes spanning the range from 0.5 mA to 2.5 mA, current frequency selected as either one of both 50 KHz to 100 KHz, current duration selected from the group consisting of current durations spanning the range from 100 msec to 500 msec, and an injection delay is selected for insertion between the end and the beginning of two successive treatment injection signals injected into two pairs of electrodes (12) out of the least one pair of electrodes as an injection delay selected from the group of delays consisting of a range spanning from 4 msec to 400 msec.

It is moreover an object of the present invention to provide a method wherein the treatment input signal is selected as an alternative current signal with predetermined signal current parameters comprising current amplitude, current frequency and current duration the treatment input signals being automatically injected sequentially into pairs of electrodes (12) chosen in predetermined sequence from an array of 24 electrodes.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIG. 1 is a block diagram of the constituents related to the method of the disclosed invention, FIG. 2 is a more detailed block diagram of FIG. 1, FIG. 4 is a schematical partial view display pertaining of the Cranial Electric Stimulator (CES) shown in FIG. 1, and FIG. 5 is an example of a diagnosis matrix display by the CES shown in FIG. 1.

DETAILED DESCRIPTION OF PREFERRED EMBODIMENTS

Figure 3:
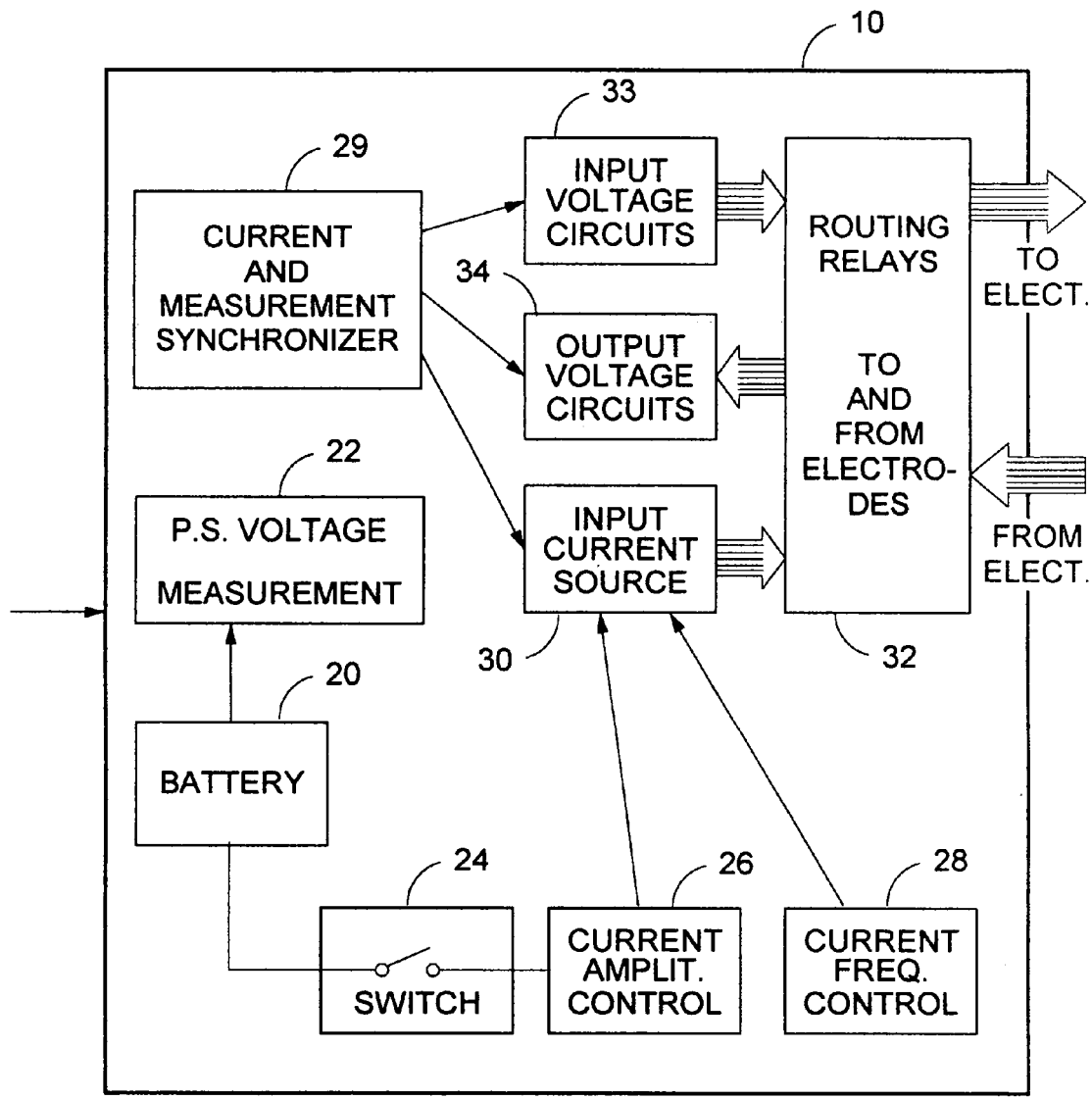
FIG. 3 shows details of the signal and routing box presented in FIGS. 1 and 2.

FIG. 1 is a block diagram of the main constituents of a method for the diagnosis, treatment and research of mental disorder. There is shown a practitioner 2 using a Cerebral Electric Stimulator 4, or CES 4 for diagnosis, or treatment, or for the research related to the skull 6 of a patient. The practitioner 2 is also referred to as a user 2, an operator 2 or a therapist 2.

As explained above, mental disorder is diagnosed as a condition imposed on the passage of an electrical input signal through a pathway in the brain. A pathway, or path, is defined for example, as running between a first electrode and a second electrode of an electrode pair. Once detected, such a condition is relieved by injection of treatment input signal. A condition is for example, an increased resistance or an increased conductivity over a path.

The CES 4 comprises mainly a workstation 8, a Signal and Routing Box 10 (SRB 10) and an array of cranial electrodes 12 affixed to the skull 6 of the patient. Furthermore, the CES 4 allows the generation of predetermined signals featuring low current amplitudes, chosen frequencies and short signal durations.

Signals from the SRB 10 are injected via the array of 24 electrodes positioned in predetermined locations on the skull 6 of the patient, and from there into the brain. With the CES 4, it is possible to measure between the two electrodes of any pair of electrodes, such signal parameters as, for example, impedance, voltage, resistance, or current. A measurement taken across a pair of electrodes is considered as being representative of a measurement along a path crossing the brain from one electrode to the other. In turn, a path between two electrodes is representative of a region of the brain.

There are at least four different modes in which the CES 4 operates: first a patient diagnosis mode, second a patient treatment mode, third a research mode and fourth a test mode, all of which are described below.

FIG. 2 depicts a preferred embodiment 100 showing more details about the CES 4, and the distribution of the array of electrodes 12, still in block-diagram form. The same numerals are used to indicate the same elements in all the drawings.

Electrodes

With reference to the FIGS. 1 and 2, the electrodes 12 are depicted as an array of 24 electrodes distributed on the skull 6 of the patient. Evidently, the array may comprise any suitable and practical number of electrodes and different distributions. Cranial electrodes are well known in the art and need no further description. Methods, known to the art, such as a helmet or the like, ensure the fast and precise affixation of the configuration of electrodes 12 on the skull 6 of the patient.

In FIG. 2 the array of electrodes 12 includes 24 electrodes, starting with first the electrode being referred to as E1 and ending with the last electrode, shown as E24. The distribution of electrodes 12 features four columns and six rows, each column running from the forehead to the neck and each row crossing the skull from one side of the head to the other. The first electrode 12 of each column of electrodes, numbered E1, E7, E13 and E19, is adjacent the forehead while the last electrode of each column of electrodes, designated as E6, E12, E18 and ending with E24, is proximate the neck. The first column of electrodes 12, starting with electrode E1 to electrode E6, is emplaced on the left side of the head whereas the fourth column of electrodes, with electrodes numbered from E18 to E24 is attached to the right side of the skull.

The distribution of the electrodes 12 is symmetric, according to the symmetry of the skull, as shown by the dash-dot symmetry line indicated as CL in FIG. 2. With respect to that symmetry, it is possible to define an "opposite" electrode. This definition is necessary for the description presented below.

For example, the upper, rightmost electrode E19 is considered as the opposite of the electrode E1. In the same manner, the electrode E12 has an opposite electrode E18. An electrode and its opposite are thus found on the same row and each one of both electrodes is located in a column equidistant from the line of symmetry CL but on opposite sides thereof. The same definition is also valid for the two electrodes in a pair of electrodes. Other definitions of opposite electrodes for a symmetric or asymmetric array electrodes are evidently possible.

For instrument control purposes, the identity and designation of the opposite electrode 12 is derived either from a look-up table, or by an algorithm, or by any other means known to the art.

In a table, the opposite electrode is listed against the injecting electrode. For an algorithm, advantage is taken from the symmetric distribution of the electrodes 12 on the skull 6 of the patient. Each electrode is related to its location in the distribution matrix of 6 rows with 4 columns. In the matrix of element $D(r, c)$ with r for row numbers and c for column number, the row number remains the same for the opposite electrode. The columns of the distribution matrix, are symmetrically disposed relative to the line CL seen in FIG. 2. Thereby, the first leftmost column always toggles with the last rightmost column and vice-versa. The same toggling mechanism is also valid for the second and third columns: the second column toggles with the third one, and vice-versa.

It is noted that the array of cranial electrodes 12 is the same for the diagnosis, treatment and research mode of operation of the CES 4, and if desired, also for the research mode. The same electrodes 12 are used for both input and output purposes since they inject signals into the skull 6 and retrieve signals from the skull. A harness of cables, or if desired wireless communication, couple each single electrode 12 to the Signal and Routing Box 10, or SRB 10.

Signal and Routing Box

The SRB 10 is a signal generator and signal routing circuitry operating under command of the workstation 8. The power supply of the SRB 10 is either a battery shown below as an example, or the mains, thus an electricity supply circuit via an isolation transformer (not shown in FIG. 2) all according to safety regulations. FIG. 2 shows one battery 20, in this case, a 9-volt battery, but more batteries may be utilized. Energy from the power supply is the source for the generation of selected sinusoidal alternative current signals possessing predetermined characteristics with parameters such as current frequency, current amplitude and signal duration, to be injected into the skull via the electrodes 12, for patient diagnosis, patient treatment, research and testing.

The sinusoidal signals generated by the SRB 10 provide a discretely selectable current frequency ranging from the 10 Hz to 500 Hz and from 10 to 100 KHz, with current-steps spanning from 50 to 500 microA and from 1 to 3 mA. Signal duration lasts from 2 to 500 msec.

For example, in the patient diagnosis mode, the SRB 10 may be set to generate an input signal of 0.5 mA at a frequency of 25 KHz for as long as 10 msec, via a first pair of electrodes, say E1 and E2. After 5 msec from the start of the signal injection, the workstation 8 commands sampling and measurement of the voltage across the same first pair of electrodes. A measurement is defined, for example, as the average of three samplings. In parallel, the voltage induced by the signal's input in the first pair of electrodes is also sampled and measured in the opposite pair of electrodes, defined as electrodes, E19 and E20, as by the explanations given above. These electrodes are sampled and measured, preferably 7 msec after the beginning of the injection of the signal. This sequence of injection, measurement of voltage over the injection electrodes 12 and of measurement of induced voltage is repeated sequentially either for a portion only or preferably for all the possible combinations of pairs of electrodes 12 of the array and for their opposite electrodes.

Although the commands for the operation of the CES 4 emanate from the workstation 8, all the injected input signals are generated by the SRB 10, which also routes the input signals to the electrodes 12 and returns the output signals from the skull 6 to the workstation 8 for measurement, processing, display, recording and storage.

FIG. 3 illustrates a schematic layout of the SRB 10. A current amplitude controller 26 and a current frequency controller 28 feed the input current source 30 with amplitude and frequency regulated signals. These regulated signals are kept within narrow tolerances to ascertain the well being and safety of the patient. The input signals are forwarded by the input current source 30 to the routing relays 32 and from there to the array of electrodes 12. A software computer program stored on magnetic media is run by the PC 14 to command routing of the regulated signals to selected pairs of electrodes from the array of electrodes 12.

As mentioned above, in all the modes of operation, the same couple of electrodes 12 not only injects but also retrieves output signals. For example, after an input current signal is injected via one pair of electrodes 12, a response voltage signal is sensed and returned from that same one pair of electrodes 12 via the routing relays 32 for measurement by the PC 14. A current and measurement synchronizer 29 coordinates the various injection and measurement activities of the input current source 30, the voltage input circuits 33 and the voltage output circuits 34. Signals induced in a pair of electrodes 12 other than the signal-injecting pair of electrodes, may also be measured. The routing relays will respond to commands from the PC 14 and route induced signals via the output voltage circuits 34 to the PC 12, for reading thereof.

The SRB 10 generates signals from a stabilized oscillator not shown in FIG. 3, the output of which may be switched-off by an external command signal, sent from the PC 14, for example. The oscillator is connected to the controlled current amplifier 26. Finally, the: SRB 10 rectifies injected input and retrieved output signals to allow readings by the PC 14.

As usual with medical equipment, a Test Function is continuously operated, by the PC 14 to check the operational status capability of the SRB 10, including a visual feedback for the practitioner 2. Operations of the CES cease immediately and automatically at the first hint to any clue of a potentially hazardous situation.

The PC 14 thus controls and commands the SRB 10 to generate signals and route such signals to and from selected electrode pairs 12, in all four modes of operation of the CES.

If desired, the SRB 10 is implemented to generate alternative current signals with the following discrete parameters.

Current amplitude: 50; 100 microA and 0.5; 1; 2.5 and 3 mA.

Current frequency: 10; 50; 100; 500 Hz and 10; 25; 50 and 100 KHz.

Current duration: 2, 10, 100, 250, and 500 msec.

Taking advantage of these parameters, an injected diagnostic signal may be configured as follows. A current with an amplitude of 0.5 mA and a frequency of 25 KHz is injected for 10 msec over a first pair of electrodes 12. After 5 msec from the onset of the current, a voltage reading is taken over the injecting pair of electrodes 12, or more precisely, the average of three voltage samplings is read. Then, 7 msec after the beginning of the current injection, a voltage reading over the opposite pair of electrodes 12 is taken, this being again, an average of three samplings. Following the end of the 10 msec current injection, a pause of 40 msec separates the end of the first signal injection from the next signal injection.

Workstation

Referring to FIG. 3, the workstation 8 features a PC 14 with standard hardware components such as one or more input devices 16, like a keyboard and a mouse, and at least one output device 18 such as a display screen and a printer. In addition, there is an I/O board not shown in FIG. 3 with at least four analog input ports with a range from 0 to 10 Volts. Furthermore, the PC 14 includes a memory 15 in which preloaded software computer programs are stored and for saving data and measurements made in any one of the operation modes of the CES 4. The computer programs are run by the PC 14 and are dedicated to the operation of the CES.

Four input ports are connected to A/D components for the conversion of derived, or output voltage from analog to digital signals, to enable measurement by the PC 14. One pair of input ports is dedicated to one pair of electrodes 12. The other pair of input ports is linked to the terminals of the battery 20.

Some 32 I/O channels, controlled by the PC 14, are employed for the command and operation of the circuitry of the SRB 10. A set of three clocks control the input voltage with one pair of clocks being dedicated to A/D sampling.

With reference to FIG. 2, the workstation 8 is operated interactively by the practitioner 2 via a set of menus presented on the output device 18, such as a display screen. Response commands are entered by the practitioner 2 via the input device 16, like a keyboard and/or a mouse.

The managerial procedures regarding medical sessions with a patient are taken care of by a menu-driven process in a manner well known in the art. These managerial procedures start by recording aspects of the planned activity, of the identity of both the practitioner 2 and the patient, of dates, times, medical details and annotations, and need not to be described.

Most often, the practitioner 2 chooses either the patient diagnosis mode or the patient treatment mode. In the patient diagnosis mode, the practitioner 2 is presented with a menu of options and commands from which he may pick a choice. Predetermined parameters are different in both diagnosis and treatment mode. In the patient diagnosis mode, the signal injection time is set to 10 msec, with 40 msec between each successive signal injection, and the current amplitude is preset to 0.5 mA at a current frequency of 25 KHz.

Patient Diagnosis Mode

The patient diagnosis mode calls for the injection of signals into successive pairs of electrodes 12 chosen from all the electrode-pair combinations possible out of the array of electrodes 12. For example, according to FIG. 2, into a first pair of electrodes, designated as E1 and E2, a signal of 0.5 mA at 25 KHz is injected for 10 msec. After 5 msec from the beginning of the signal injection, the voltage over the first pair of electrodes E1 and E2 is sampled, averaged, labeled as VIN1;2 and saved in memory 15. Next, about 7 msec from the start of the signal injection, the induced voltage over the opposite pair of electrodes E19 and E20, is sampled, averaged and saved in memory 15 as VOUT 19;20. At the end of the patient diagnosis signal injection, lasting 10 msec in total, a delay of 40 msec separates the first signal injection from the next one.

The patient diagnosis mode is driven by the dedicated computer program software preloaded into the memory 15 of the PC 14. The dedicated computer program operated by the PC 14 commands the SRB 10 to generate the predetermined patient diagnosis signals for injection into all the possible combination of pairs of electrodes 12 and to derive samplings from opposite pairs of electrodes. These samplings are returned to the PC 14 where measurements are taken, and where those measurements are labeled with a designation according to the electrode-pair involved, and if desired, also stored.

Once the first signal injection cycle is accomplished, thus after 10 msec of injection plus 40 msec of delay, totaling 50 msec, the second signal injection starts. Since an array of electrodes 12 consisting of a total of 24 electrodes allows for 276 different electrode-pair combinations, [with n=24 and the combinations totaling n(n−1):2] the whole patient diagnosis procedure will last 276×0.05 sec=13.8 sec. It is thus possible to run a complete diagnosis procedure on a patient 2 in the remarkably short time of less than 15 seconds.

The signal injection procedure follows a predetermined sequence of electrode-pairs. For each electrode-pair, the opposite electrode-pair was defined above, but other definitions of "opposite" may be considered. Furthermore, the number of 24 electrodes in the array 12 is not a limit but a preferred embodiment. The present invention will operate well with less than, and with more than 24 electrodes.

Data Presentation

The data relevant to the patient diagnosis procedure is mapped as a diagnosis-matrix for straightforward appreciation and ease of analysis by the practitioner 2.

By way of example, a partially filled diagnosis-matrix for an array of 24 electrodes 12 is shown in FIG. 4. The first row on the top and the leftmost column of the matrix represent coordinates used to designate pairs of electrodes 12 by E number(s). Consequently, an electrode 12 from the array of electrodes 12 is indicated as En, with n running from 1 to 24 for a preferred embodiment. E1 is the first electrode 12 and E24 is the last one. In the same manner, a pair of electrodes 12 consisting of the first electrode E1 and of the second electrode E2 are indicated as E1;2.

A portion of a diagnosis-matrix with 24 rows and 24 columns for use with an array of 24 electrodes is shown in FIG. 4. Both columns and row are numbered sequentially from 1 to 24. A cell of the matrix defined by the pair of numbers representing the intersection of a row with a column is used to store a value pertaining to a pair of electrodes. For example, the cell (1,2) in the first row and the second columns, represents the pair of electrodes E1 and E2, also designated as E1;2. However, since with the present invention, signals are always measured over pairs of electrodes and since there is no pair of electrodes E1;1, the cells of the diagonal of the matrix have no significance. The array of cells [1;1, 2;2, 3;3, . . . 24;24] is therefore of no use and is indicated accordingly, for example, shown filled with the letter X.

Since the pair of electrodes E1;2 and E2;1 are identical, the signals will also be identical and there is no point in filling both matrix cells (1;2) and (2;1), on both sides of the diagonal of the matrix, with the same data. It is thus advantageous to present one kind of values above the diagonal and to display another sort of information below the diagonal of the matrix. Values in the cells above the diagonal are designated with an A, like cell A1;2 to differentiate them from data in cells bellow the diagonal, which are assigned the letter B, such as for cell B20; 19.

Because the CES is software driven, no restrictions are imposed on the flexibility of data presentation to the practitioner 2. However, it is sufficient to show the value of the injected signals only once, perhaps as a heading above the presentation matrix, since these signals are the same for all the 24 electrodes 12.

In one display mode, the cells of the matrix above the diagonal may show the value of the voltage measured across the injecting electrodes 12. In a second display mode, the practitioner 2 may be presented, still in the cells of the matrix above the diagonal, with the value of the resistance developed across the injecting pair of electrodes 12. The resistance is calculated by dividing the voltage measure over a pair of electrodes 12 by the injected current. This division is performed by the PC 14 according to Ohm's law V=IR, where V is the voltage, I the current and, R the resistance.

Conversely, to the resistance, a third display mode may exhibit the conductance, which is the inverse of the resistance. To keep the example simple, reference is made to resistance and conductance only, but impedance may be treated in the same manner. It is for the practitioner 2 to choose the preferred screen display mode by a simple request entered via the input device 16.

Even though only those cells above the diagonal of the matrix of FIG. 4, that pertain to data related to the injection signal injecting electrodes, spread over less than half of the cells of the matrix, there are still 276 cells for the practitioner 2 to consider. To facilitate the task, the data is processed by the PC 14. For example, it is feasible to highlight in each row, say by coloring in red, the cell with the highest resistance or to stress the three cells with the highest resistance, perhaps in pink. The same method may be followed, with other colors, for the cells containing the lowest resistance values. Thereby, both the value of the signals and the identity of the pair of electrodes 12 involved are pointed out. Clearly indicating outstanding data alleviates the burden on the practitioner 2 and allows him to concentrate on specific problematic areas.

Instead of emphasizing extreme values, it is evidently feasible to stress "out of norm values" or any other specifically selected group of values. Such a flexibility of choice stems from the fact that the equipment is controlled by computer programs. Therefore, different computer programs permit to highlight on the display any chosen set of data as reference information, either predetermined data stored in memory or data measured in real-time on the patient. Relative to the reference data, the operator 2 detects the abnormal measurements or response signals, pertaining to specific electrode pairs or even to regions of the skull 6.

It was explained above that after some 7 msec from the start of a signal injection over a pair of electrodes 12, that may be labeled in general as Em;n, an induced voltage is measured. That induced voltage taken across the opposite electrodes 12 is sampled, averaged, measured, displayed and saved in memory 15 as VOUT m;n, if desired.

Similarly to the method used for the presentation of the voltage measured over the pair of injecting electrodes in response to the injected signals, the induced signals are displayed below the diagonal retaining the same denomination convention. For example, a value derived from the pair of injecting electrodes E1;2 is shown in the cell designated as A1;2 of the matrix in FIG. 4. However, the induced signal, retrieved over the opposite couple of electrodes E19;20 is not displayed in the matrix cell 19;20 above the diagonal, but below the diagonal, in the cell B20;19. First, the cell A19;20 is reserved for a value from an injecting pair of electrodes 12. Second, since the pair of electrodes 19;20 is identical to the pair 20;19, advantage is taken from that symmetry. FIG. 4 depicts the injection signal values in the cells Am;n while the induced signal values are listed in the cells Bn;m.

Patient Treatment Mode

In the patient treatment mode, the signal injection time lasts for 250 msec, with a delay of 40 msec between consecutive signal injections. The current amplitude is predetermined to 1.5 mA at a current frequency of either 50 KHz or 100 KHz, according to the selection of practitioner 2. In contrast with the patient diagnosis procedure, treatment signals are injected only in discretely selected pairs of electrodes 12 specifically chosen by the practitioner 2. However, to estimate the maximum duration of a session in the patient treatment procedure, it is assumed that all 276 combinations of electrode couples are selected for injection, lasting for 0.25 sec of injection plus a delay of 0.04 sec, thus 276×0.29 sec=80.04 sec. The very short patient treatment time will never exceed 1.34 minutes.

In the patient treatment mode the practitioner 2 responds to data derived earlier in the patient diagnosis mode with the same patient, before making a decision about the therapy to be applied. Evidently, data from earlier diagnosis sessions is used in combination with information from the very last previous diagnosis session, if desired. In the same way, data referring to population groups, such as sex, age, origin may also be used for making decisions about the treatment to be applied.

In practice, the practitioner 2 first designates on a displayed matrix, the selected electrode pairs. Then, in a second step, he chooses between an injection current frequency of either 50 KHz or 100 KHz. It is possible to inject more than one pair of electrodes, and even to select a different current frequency for each selected pair. An acknowledge command followed by a start command will automatically run the patient treatment procedure. One single pair of electrodes 12 or a succession thereof, is thus operated in the patient treatment mode.

In the same way as for the patient diagnosis procedure, all the formal data, or managerial procedure, regarding the patient, the practitioner 2, the dates, time and procedure data are carefully recorded and saved.

Injected Charge

To perceive the insignificance of the charge of electricity injected into the patient and for purpose of comparison, one may consider to adopt the conventional definition of an electric charge of one Coulomb, defined as one Ampere times one second. For the diagnosis procedure therefore, the total charge of 276 injections with 0.5 mA for a duration of 10 msec, results in the minute amount of 276×0.005× 0.01=0.0138 Coulombs.

Again, in the patient treatment mode, the injected electric dose is minimal. Even if the practitioner 2 selects as much as 8 pairs of electrodes for consecutive injection, at a current amplitude of 1.5 mA for a duration of 0.25 sec, this results in a miniscule total charge of 8×0.015×0.25=0.03 Coulombs.

Research Mode

The research mode provides latitude of freedom that permits a wide variety of signal parameter choices in comparison with the predetermined parameters of the previously described modes. It should be emphasized that access to this research mode is granted according to identification and permission mechanisms established to prevent mistakes. In a preferred embodiment, this research mode may be deleted altogether, thus avoiding a situation where a patient is accidentally administered an injection signal level not conforming to the stipulations of the diagnosis or treatment mode.

In the research mode, the therapist 2 is permitted to choose between the aforementioned different values including eight current frequencies, six current amplitudes, and five different current durations. This freedom of choice is possible for both the research diagnosis mode as well as for the research treatment mode.

In practice, the operator 2 of the CES is requested to manually point-out the signal parameters selected, which are first displayed for confirmation and then stored. In the research diagnosis mode and in the research treatment mode, the same matrix display is employed as with the previously described, respectively, patient diagnosis and patient treatment mode.

Test Mode

Although automatic test commands are generated continuously during all operation modes, a separate test mode is provided to allow the operator 2 to selectively test each single function of the CES. It should be noted that in all the four operation modes, when the situation so requires, a message is sent to the operator 2 and in case of the slightest potential danger, the equipment is automatically shut-off.

Diagnosis Session

While the array of electrodes 12 is being attached to the skull 6 of the patient, the practitioner 2 handles first the managerial procedures related to the diagnosis session, Then he runs a test of the CES to confirm the safety of the equipment and gives permission to connect the array of electrodes to the SRB 10. The signal injection procedure is launched next, by which all the possible combinations of electrode-pairs are accessed in a predetermined sequence.

As a result, of the predetermined signal injection and of the measurements, the practitioner 2 is presented with a diagnosis matrix of data. To easily locate extreme values, help is provided by coloring schemes or assistance tables. The layout in black and white of such an assistance table is illustrated in FIG. 5, for 24 electrodes 12.

The retrieved data resulting from the signal injection are exhibited in many ways to assist the practitioner. The chosen configuration of display is consistent and allows the practitioner 2 to view other related data in the same display configuration. For example, it is beneficial to compare the matrix of patient diagnosis signals with matrices derived in previous patient diagnosis sessions with the same patient or even to compare with standard data matrices for populations of the same group as that of the patient. Such a population group may relate among others, to age, gender, origin, ethnic group, and the like. Armed with these tools, the practitioner 2 must now determine into which pairs of electrodes 12 to inject the treatment signals. Usually, a search is made for paths featuring a peculiar condition to the passage of an electrical signal, such as blocked paths. A blocked brain path is recognized, for example, by a high resistance between two electrodes 12. In response, in the patient treatment mode, a current is delivered on the same path, thus between those same two electrodes 12, to "unblock" a possible obstruction and restore normal conditions.

Before ending the patient diagnosis procedure, the retrieved data is carefully recorded, saved in memory 15 and may even be printed out for further study.

Treatment Session

Similarly to the diagnosis session, managerial procedures are handled in parallel to the connection of electrodes 12 to skull 6 of the patient, before running a conventional safety test. The practitioner 2 then designates on a matrix of electrodes pairs into which couples of electrodes 12 he wants to inject the treatment signals. This decision is a result from the analysis of the diagnosis results and the comparison data. In a last decision, the current frequency, either 50 or 100 KHz is selected and entered. Once the equipment acknowledges readiness to run the treatment procedure, the command to proceed may be given. The CES performs the treatment procedure covering the designated pairs of electrodes 12. As before, all pertinent data relating to the treatment session is carefully recorded and saved, in memory 15 or any other memory facility.

It will be appreciated by persons skilled in the art, that the present invention is not limited to what has been particularly shown and described hereinabove.

For example, the detection of a condition pertaining to the passage of an electrical signal via an electrical paths may be achieved by detection over an area covered by a plurality of electrodes. Likewise, the treatment is, if desired, accomplished by injection of treatment signals into a region covered by more than two electrodes. Rather, the scope of the present invention is defined by the appended claims and includes both combinations and subcombinations of the various features described hereinabove as well as variations and modifications thereof which would occur to persons skilled in the art upon reading the foregoing description.

The invention claimed is:

1. A method for diagnosing a mental disorder by injecting electric input signals into and measuring electric output signals from a brain via electrodes arranged in an array comprising a symmetrical electrode distribution attached to a skull of a patient, the method comprising the steps of:
operating a diagnostic mode comprising automatic sequential injection of diagnostic input signals in a predetermined sequence into combinations of pairs of electrodes chosen from the array of electrodes,
measuring output signals from each combination of pairs of electrodes, and
displaying the measured output signals in association with the combination of pairs of electrodes for detection and diagnosis of a mental disorder when operating in a diagnostic mode.

2. The method according to claim 1, wherein:
electrodes of the array of electrodes are identified by designations including a designation of a row, a column, an electrode pair, an opposite electrode pair, an electrode and an opposite electrode.

3. The method according to claim 2, wherein the array of electrodes comprises at least 4 electrodes and at most 60 electrodes operative in all possible combinations of electrode pairs.

4. The method according to claim 2, wherein the array of electrodes includes 24 electrodes operative in 276 combinations of pairs of electrodes.

5. The method according to claim 1, wherein:
the diagnostic input signal is an alternative current signal with predetermined signal current parameters comprising current amplitude, current frequency and current duration, and
the output signals are measured from each combination of pairs of electrodes and from each opposite electrode pair.

6. The method according to claim 5, wherein:
the current amplitude of the diagnostic input signal is selected from the group consisting of current amplitudes spanning the range from 0.1 mA to 5 mA in association with a current frequency of between 16 KHz and 250 KHz.

7. The method according to claim 5, wherein:
the current frequency of the diagnostic input signal is selected from the group consisting of current frequencies spanning the range from 16 KHz to 250 KHz.

8. The method according to claim 5, wherein:
the current duration of the diagnostic input signal is selected from the group consisting of current durations spanning the range from 1 msec to 500 msec, in association with a current frequency of between 16 KHz and 250 KHz.

9. The method according to claim 5, wherein:
the diagnostic input signal is selected to comprise a current amplitude of 0.5 mA, a current frequency of 25 KHz and a current duration of 10 msec.

10. The method according to the claim 5, wherein:
each injection signal for injection into combinations of pairs of electrodes has an injection signal beginning and an Injection signal end, and
an injection delay for insertion between the injection signal end and the injection signal beginning of two successive diagnostic injection signals is chosen as a diagnostic injection delay selected from the group of delays consisting of a range spanning from 4 msec to 400 msec.

11. The method according to claim 10, wherein:
the injection delay duration is selected as 40 msec.

12. The method according to claim 5, wherein:
an output signal is measured over the pair of electrodes selected for signal injection within a specific injection delay after beginning signal injection but before ending signal injection.

13. The method according to claim 12, wherein:
the injection delay is selected as 5 msec.

14. The method according to claim 5, wherein:
an output signal is measured over the pair of electrodes opposite to the pair of electrodes injected with the diagnostic signal injection within a specific opposite delay after starting but before ending signal injection.

15. The method according to claim 14, wherein:
the opposite delay is selected as 7 msec.

16. The method according to claim 1, wherein automatically sequentially injecting a diagnostic input signal in pairs of electrodes includes:
selecting a first pair of electrodes for injecting therein an electrical diagnostic input signal; and
selecting a next electrode-pair for injecting therein the injection signal, and successively injecting the injection signal in all possible combinations of electrode-pairs possible out of the array of electrodes.

17. The method according to the claim 5, wherein:
diagnostic output signals are measured in association with diagnostic input signals in dimensions selected from the group of dimensions consisting of voltage, frequency, impedance, resistance and conductance.

18. The method according to claim 17, wherein:
the diagnostic output signals are processed for display, and
diagnostic output signals are displayed in association with an electrode pair designation indicating each combination of electrode pairs for detection and diagnosis of mental disorder.

19. The method according to claim 16, wherein:
multiplication of the current amplitude of the diagnostic input signals injected over an array of 24 electrodes into the skull of a patient by the duration of current injection, results in a product smaller than 0.015.

20. The method according to claim 1, further comprising:
operating a treatment mode, wherein operation of the treatment mode includes injecting a treatment input signal in at least one pair of electrodes chosen in response to detection and diagnosis achieved in the diagnostic mode.

21. The method according to claim 20 wherein:
the treatment input signal is selected as an alternative current signal with predetermined signal current parameters comprising current amplitude, current frequency and current duration, and
the treatment input signal is selected in response to a diagnostic output signal.

22. The method according to claim 21, wherein:
the current amplitude of the treatment input signal is selected from the group consisting of current amplitudes spanning the range from 0.5 mA to 2.5 mA with a frequency in the range of 16 KHz to 250 KHz.

23. The method according to claim 21, wherein:
the current frequency of the treatment input signal is in the range of 50 KHz to 100 KHz.

24. The method according to claim 21, wherein:
the current duration of the treatment input signal is selected from the group consisting of current durations spanning the range from 100 msec to 500 msec, and
the current frequency of the treatment input signal is in the range of 50 KHz to 100 KHz.

25. The method according to claim 21, wherein:
the treatment input signal is selected to comprise a current amplitude of 1.5 mA, a current frequency in the range of 50 and 100 KHz and a current duration of 250 msec.

26. The method according to claim 21 wherein:
each treatment input signal for injection into combinations of pairs of electrodes has an input signal beginning and an input signal end, and
an injection delay for insertion between the end and the beginning of two successive treatment input signals injected into two pairs of electrodes out of the at least one pair of electrodes is chosen as an injection delay selected from the group of delays consisting of a range spanning from 4 msec to 400 msec.

27. The method according to claim 26, wherein:
the treatment injection delay duration is selected as 40 msec.

28. The method according to claim 21 wherein:
the treatment input signal is selected as an alternative current signal with predetermined signal current parameters including current amplitude, current frequency and current duration for automatic sequential injection of the treatment input signals in pairs of electrodes chosen in predetermined sequence and combination from the array of electrodes.

29. The method according to claim 28, wherein:
the treatment input signal is selected to include a current amplitude of 1.5 mA, a current frequency in the range of 50 and 100 KHz, a current duration of 250 msec, and a treatment injection delay duration of 40 msec.

30. The method according to claim 1, further comprising:
operating a research mode, wherein the research mode comprises injecting either one of both a research diagnosis input signal and a research treatment input signal in at least one pair of electrodes, and measuring output signals from each combination of pairs of electrodes.

31. The method according to claim 30, wherein:
the research diagnostic input signal is selected as an alternative current signal with predetermined signal current parameters comprising current amplitude, current frequency and current duration, and
research output signals are measured over the electrodes pair injected with the research diagnostic input signal and over the opposite electrode pair.

32. The method according to claim 31, wherein:
the current amplitude of the research diagnosis input signal is selected from the group consisting of 50 microA, 100 microA, 0.5 mA, 1 mA, 2.5 mA and 3 mA and in the frequency range of 16 KHz to 250 KHz.

33. The method according to claim 31, wherein:
the current frequency of the research diagnosis input signal is selected from the group consisting of 25 KHz, 50 KHz, and 100 KHz.

34. The method according to claim 31, wherein:
the current duration of the research diagnosis input signal is selected from the group consisting of 2 msec, 10 msec, 100 msec, 250 msec and 500 msec and in the frequency range of 16 KHz to 25 KHz.

35. The method according to claim 31, wherein:
an injection delay for insertion between the end and the beginning of two successive diagnostic injection signals is selected from the group of delays consisting of a range spanning from 4 msec to 400 msec.

36. The method according to claim 31, wherein:
a research output signal is measured over the pair of electrodes selected for research signal injection within a specific injection delay after starting but before ending of the research signal injection.

37. The method according to claim 31, wherein:
a research output signal is measured over the pair of electrodes opposite to the pair of electrodes injected with the research signal injection within a specific opposite delay after starting but before ending of the signal injection.

38. The method according to claim 31, wherein:
a first pair of electrodes is selected for injecting therein a research diagnosis signal, and a next electrode-pair is selected for injecting therein the research injection signal, and successively injecting the research injection signal in all the combinations of electrode-pairs possible out of the array of electrodes.

39. The method according to claim 31, wherein:

research diagnosis output signals are measured in dimensions selected from the group of dimensions consisting of voltage, frequency, impedance, and resistance and conductance in the frequency range is selected from 16 KHz to 250 KHz.

40. The method according to claim 39, wherein:

the research diagnosis output signals are processed for display, and the research diagnosis output signals are displayed in association with research diagnosis input signals and with an electrode pair designation for detection and diagnosis of mental disorder.

* * * * *